(12) United States Patent
Bae et al.

(10) Patent No.: US 10,390,955 B2
(45) Date of Patent: Aug. 27, 2019

(54) BONE IMPLANTS

(71) Applicant: ENGAGE MEDICAL HOLDINGS, LLC, Los Angeles, CA (US)

(72) Inventors: Hyun Bae, Santa Monica, CA (US); Daniel F. Justin, Orlando, FL (US); Edwin Su, Scarsdale, NY (US)

(73) Assignee: ENGAGE MEDICAL HOLDINGS, LLC, Los Angeles, CA (US)

( * ) Notice: Subject to any disclaimer, the term of this patent is extended or adjusted under 35 U.S.C. 154(b) by 0 days.

(21) Appl. No.: 15/713,594

(22) Filed: Sep. 22, 2017

(65) Prior Publication Data

US 2018/0078374 A1 Mar. 22, 2018

Related U.S. Application Data

(60) Provisional application No. 62/398,259, filed on Sep. 22, 2016.

(51) Int. Cl.
*A61F 2/28* (2006.01)
*A61B 17/80* (2006.01)
*A61F 2/30* (2006.01)
*A61F 2/36* (2006.01)
*A61F 2/32* (2006.01)

(52) U.S. Cl.
CPC ............ *A61F 2/28* (2013.01); *A61B 17/8095* (2013.01); *A61F 2/3094* (2013.01); *A61F 2/30734* (2013.01); *A61F 2/30749* (2013.01); *A61F 2/32* (2013.01); *A61F 2/3601* (2013.01); *A61L 2430/02* (2013.01)

(58) Field of Classification Search
CPC ...... A61F 2/28; A61F 2/30749; A61F 2/4465; A61F 2/4601; A61F 2002/30281; A61B 17/8095

See application file for complete search history.

(56) References Cited

U.S. PATENT DOCUMENTS

| | | |
|---|---|---|
| 3,486,505 A | 12/1969 | Morrison |
| 3,641,590 A | 2/1972 | Michele |
| 3,650,309 A | 3/1972 | Neuschotz |
| 3,842,825 A | 10/1974 | Wagner |
| 3,848,276 A | 11/1974 | Martinez |
| 3,882,917 A | 5/1975 | Orlomoski |
| 3,896,504 A | 7/1975 | Fischer |
| 3,907,017 A | 9/1975 | Stanwick |
| 3,927,503 A | 12/1975 | Wilson |
| 4,011,602 A | 3/1977 | Rybicki |
| 4,047,524 A | 9/1977 | Hall |

(Continued)

FOREIGN PATENT DOCUMENTS

| | | |
|---|---|---|
| EP | 0179695 | 4/1986 |
| EP | 1327423 | 7/2003 |

(Continued)

*Primary Examiner* — Brian A Dukert
(74) *Attorney, Agent, or Firm* — Maywood IP Law; G. Jo Hays; David W. Meibos

(57) ABSTRACT

A bone implant system to correct bone abnormalities and/or change bone morphology includes a bone implant and one or more bone anchors. The bone implant may be generally wedge shaped, and may be formed of one or more conjoined crescent shapes. The bone anchor slidingly engages the bone implant and the bone to provide fixation.

10 Claims, 12 Drawing Sheets

(56) References Cited

U.S. PATENT DOCUMENTS

| | | |
|---|---|---|
| 4,260,005 A | 4/1981 | Stencel |
| 4,349,955 A | 9/1982 | Keen |
| 4,355,429 A | 10/1982 | Mittelmeier |
| 4,454,875 A | 6/1984 | Pratt |
| 4,484,570 A | 11/1984 | Sutter |
| 4,501,269 A | 2/1985 | Bagby |
| D281,814 S | 12/1985 | Pratt |
| 4,570,623 A | 2/1986 | Ellison |
| 4,611,581 A | 9/1986 | Steffee |
| 4,642,869 A | 2/1987 | Muller |
| 4,681,589 A | 7/1987 | Tronzo |
| 4,716,893 A | 1/1988 | Fischer |
| 4,743,256 A | 5/1988 | Brantigan |
| 4,743,262 A | 5/1988 | Tronzo |
| 4,764,067 A | 8/1988 | Kawashima |
| 4,820,305 A | 4/1989 | Harms |
| 4,834,757 A | 5/1989 | Brantigan |
| 4,838,891 A | 6/1989 | Branemark |
| 4,848,328 A | 7/1989 | Laboureau |
| 4,865,607 A | 9/1989 | Witzel |
| 4,874,389 A | 10/1989 | Downey |
| 4,930,962 A | 6/1990 | Reynolds |
| 4,946,378 A | 8/1990 | Hirayama |
| 4,957,496 A | 9/1990 | Schmidt |
| 5,002,576 A | 3/1991 | Fuhrmann |
| 5,019,103 A | 5/1991 | Van Zile |
| 5,053,038 A | 10/1991 | Sheehan |
| 5,074,880 A | 12/1991 | Mansat |
| 5,147,361 A | 9/1992 | Ojima |
| 5,163,960 A | 11/1992 | Bonutti |
| 5,192,324 A | 3/1993 | Kenna |
| 5,192,327 A | 3/1993 | Brantigan |
| 5,306,309 A | 4/1994 | Wagner |
| 5,314,477 A | 5/1994 | Marnay |
| 5,352,229 A | 10/1994 | Goble |
| 5,366,479 A | 11/1994 | McGarry |
| 5,431,658 A | 7/1995 | Moskovich |
| 5,443,515 A | 8/1995 | Cohen |
| 5,449,359 A | 9/1995 | Groiso |
| 5,454,814 A | 10/1995 | Comte |
| D364,462 S | 11/1995 | Michelson |
| 5,507,816 A | 4/1996 | Bullivant |
| 5,514,180 A | 5/1996 | Heggeness |
| D378,409 S | 3/1997 | Michelson |
| 5,609,635 A | 3/1997 | Michelson |
| 5,658,337 A | 8/1997 | Kohrs |
| 5,660,188 A | 8/1997 | Groiso |
| 5,683,394 A | 11/1997 | Rinner |
| 5,702,449 A | 12/1997 | McKay |
| 5,709,683 A | 1/1998 | Bagby |
| 5,713,899 A | 2/1998 | Marnay |
| 5,769,852 A | 6/1998 | Brånemark |
| 5,772,661 A | 6/1998 | Michelson |
| 5,776,199 A | 7/1998 | Michelson |
| 5,776,202 A | 7/1998 | Copf |
| 5,788,701 A | 8/1998 | McCue |
| 5,800,550 A | 9/1998 | Sertich |
| 5,853,414 A | 12/1998 | Groiso |
| 5,860,973 A | 1/1999 | Michelson |
| 5,885,287 A | 3/1999 | Bagby |
| 5,893,889 A | 4/1999 | Harrington |
| 5,893,890 A | 4/1999 | Pisharodi |
| 5,947,999 A | 9/1999 | Groiso |
| 5,993,476 A | 11/1999 | Groiso |
| 6,039,762 A | 3/2000 | McKay |
| 6,059,787 A | 5/2000 | Allen |
| 6,063,121 A | 5/2000 | Xavier |
| 6,080,155 A | 6/2000 | Michelson |
| 6,096,080 A | 8/2000 | Nicholson |
| 6,102,949 A | 8/2000 | Biedermann |
| 6,113,638 A | 9/2000 | Williams |
| 6,120,503 A | 9/2000 | Michelson |
| 6,136,001 A | 10/2000 | Michelson |
| 6,159,214 A | 12/2000 | Michelson |
| 6,224,607 B1 | 5/2001 | Michelson |
| 6,235,059 B1 | 5/2001 | Benezech |
| 6,241,769 B1 | 6/2001 | Nicholson |
| 6,241,770 B1 | 6/2001 | Michelson |
| 6,270,498 B1 | 8/2001 | Michelson |
| 6,302,914 B1 | 10/2001 | Michelson |
| 6,309,421 B1 | 10/2001 | Pisharodi |
| 6,325,805 B1 | 12/2001 | Ogilvie |
| 6,336,928 B1 | 1/2002 | Guerin |
| 6,364,880 B1 | 4/2002 | Michelson |
| 6,402,785 B1 | 6/2002 | Zdeblick |
| 6,413,278 B1 | 7/2002 | Marchosky |
| 6,432,107 B1 | 8/2002 | Ferree |
| 6,436,098 B1 | 8/2002 | Michelson |
| 6,447,524 B1 | 9/2002 | Knodel |
| 6,447,544 B1 | 9/2002 | Michelson |
| 6,447,546 B1 | 9/2002 | Bramlet |
| 6,458,159 B1 | 10/2002 | Thalgott |
| 6,478,800 B1 | 11/2002 | Fraser |
| 6,485,517 B1 | 11/2002 | Michelson |
| 6,506,216 B1 | 1/2003 | McCue |
| 6,537,320 B1 | 3/2003 | Michelson |
| 6,558,423 B1 | 5/2003 | Michelson |
| 6,558,424 B2 | 5/2003 | Thalgott |
| 6,582,468 B1 | 6/2003 | Gauchet |
| 6,599,294 B2 | 7/2003 | Fuss |
| 6,610,093 B1 | 8/2003 | Pisharodi |
| 6,620,198 B2 | 9/2003 | Burstein |
| 6,652,533 B2 | 11/2003 | O'Neil |
| 6,679,887 B2 | 1/2004 | Nicholson |
| 6,716,245 B2 | 4/2004 | Pasquet |
| 6,726,720 B2 | 4/2004 | Ross |
| 6,740,118 B2 | 5/2004 | Eisermann |
| 6,743,256 B2 | 6/2004 | Mason |
| 6,746,450 B1 | 6/2004 | Wall |
| 6,755,841 B2 | 6/2004 | Fraser |
| 6,767,356 B2 | 7/2004 | Kanner |
| 6,767,367 B1 | 7/2004 | Michelson |
| 6,770,074 B2 | 8/2004 | Michelson |
| 6,770,096 B2 | 8/2004 | Bolger |
| 6,773,437 B2 | 8/2004 | Ogilvie |
| 6,800,093 B2 | 10/2004 | Nicholson |
| 6,802,863 B2 | 10/2004 | Lawson |
| 6,827,740 B1 | 12/2004 | Michelson |
| 6,835,208 B2 | 12/2004 | Marchosky |
| 6,849,093 B2 | 2/2005 | Michelson |
| 6,875,213 B2 | 4/2005 | Michelson |
| 6,923,810 B1 | 8/2005 | Michelson |
| 6,923,830 B2 | 8/2005 | Michelson |
| 6,926,718 B1 | 8/2005 | Michelson |
| 6,942,698 B1 | 9/2005 | Jackson |
| 6,969,390 B2 | 11/2005 | Michelson |
| 6,972,035 B2 | 12/2005 | Michelson |
| 6,981,975 B2 | 1/2006 | Michelson |
| 6,989,031 B2 | 1/2006 | Michelson |
| 7,033,394 B2 | 4/2006 | Michelson |
| 7,041,135 B2 | 5/2006 | Michelson |
| 7,044,972 B2 | 5/2006 | Mathys, Jr. |
| 7,048,766 B2 | 5/2006 | Ferree |
| 7,056,344 B2 | 6/2006 | Huppert |
| 7,056,345 B2 | 6/2006 | Kuslich |
| 7,060,097 B2 | 6/2006 | Fraser |
| 7,066,961 B2 | 6/2006 | Michelson |
| 7,083,623 B2 | 8/2006 | Michelson |
| 7,083,652 B2 | 8/2006 | McCue |
| 7,087,082 B2 | 8/2006 | Paul |
| 7,112,206 B2 | 9/2006 | Michelson |
| 7,115,146 B2 | 10/2006 | Boyer, II |
| 7,118,580 B1 | 10/2006 | Beyersdorff |
| 7,128,761 B2 | 10/2006 | Kuras |
| 7,163,560 B2 | 1/2007 | Mason |
| 7,166,110 B2 | 1/2007 | Yundt |
| 7,166,129 B2 | 1/2007 | Michelson |
| 7,169,182 B2 | 1/2007 | Errico |
| 7,204,852 B2 | 4/2007 | Marnay |
| 7,235,101 B2 | 6/2007 | Berry |
| 7,235,105 B2 | 6/2007 | Jackson |
| 7,255,698 B2 | 8/2007 | Michelson |
| 7,320,707 B2 | 1/2008 | Zucherman |
| 7,326,248 B2 | 2/2008 | Michelson |

(56) References Cited

U.S. PATENT DOCUMENTS

| | | |
|---|---|---|
| 7,331,995 B2 | 2/2008 | Eisermann |
| 7,357,817 B2 | 4/2008 | D'Alessio, II |
| 7,364,589 B2 | 4/2008 | Eisermann |
| 7,396,365 B2 | 7/2008 | Michelson |
| 7,462,196 B2 | 12/2008 | Fraser |
| 7,481,830 B2 | 1/2009 | Wall |
| 7,481,832 B1 | 1/2009 | Meridew |
| D586,915 S | 2/2009 | Grim |
| 7,491,205 B1 | 2/2009 | Michelson |
| 7,503,933 B2 | 3/2009 | Michelson |
| 7,503,934 B2 | 3/2009 | Eisermann |
| 7,503,935 B2 | 3/2009 | Zucherman |
| D594,986 S | 6/2009 | Miles |
| 7,540,882 B2 | 6/2009 | Michelson |
| 7,556,650 B2 | 7/2009 | Collins |
| 7,572,293 B2 | 8/2009 | Rhodes |
| 7,588,600 B2 | 9/2009 | Benzel |
| 7,594,931 B2 | 9/2009 | Louis |
| 7,611,538 B2 | 11/2009 | Belliard |
| 7,658,766 B2 | 2/2010 | Melkent |
| 7,695,516 B2 | 4/2010 | Zeegers |
| 7,749,271 B2 | 7/2010 | Fischer |
| 7,763,076 B2 | 7/2010 | Navarro |
| 7,780,676 B2 | 8/2010 | Lakin |
| 7,837,732 B2 | 11/2010 | Zucherman |
| 7,850,791 B2 | 12/2010 | Quadakkers |
| 7,883,510 B2 | 2/2011 | Kim |
| 7,887,563 B2 | 2/2011 | Cummins |
| 7,896,919 B2 | 3/2011 | Belliard |
| 7,909,871 B2 | 3/2011 | Abdou |
| 7,918,891 B1 | 4/2011 | Curran |
| 7,966,799 B2 | 6/2011 | Morgan |
| 8,021,403 B2 | 9/2011 | Wall |
| 8,034,076 B2 | 10/2011 | Criscuolo |
| 8,062,297 B2 | 11/2011 | Faillace |
| 8,100,972 B1 | 1/2012 | Bruffey |
| 8,100,974 B2 | 1/2012 | Duggal |
| 8,105,389 B2 | 1/2012 | Berelsman |
| 8,123,757 B2 | 2/2012 | Zalenski |
| 8,133,283 B2 | 3/2012 | Wilson |
| 8,157,865 B2 | 4/2012 | Hochschuler |
| 8,287,572 B2 * | 10/2012 | Bae ............... A61B 17/846 606/279 |
| 8,491,598 B2 | 7/2013 | Crook |
| 8,500,747 B2 | 8/2013 | DeRidder |
| 8,636,191 B2 | 1/2014 | Meagher |
| 8,747,412 B2 | 6/2014 | Bae |
| 8,808,294 B2 | 8/2014 | Fox |
| 9,254,130 B2 | 2/2016 | Hollis |
| 9,480,511 B2 | 11/2016 | Butters |
| 9,925,051 B2 | 3/2018 | Bae |
| 10,238,382 B2 | 3/2019 | Terrill |
| 10,238,426 B2 | 3/2019 | Butters |
| 10,245,090 B2 | 4/2019 | Hollis |
| 2001/0000532 A1 | 4/2001 | Michelson |
| 2001/0010001 A1 | 7/2001 | Michelson |
| 2001/0010002 A1 | 7/2001 | Michelson |
| 2001/0010020 A1 | 7/2001 | Michelson |
| 2001/0037154 A1 | 11/2001 | Martin |
| 2001/0047207 A1 | 11/2001 | Michelson |
| 2001/0047208 A1 | 11/2001 | Michelson |
| 2002/0004683 A1 | 1/2002 | Michelson |
| 2002/0035400 A1 | 3/2002 | Bryan |
| 2002/0049447 A1 | 4/2002 | Li |
| 2002/0091390 A1 | 7/2002 | Michelson |
| 2002/0095155 A1 | 7/2002 | Michelson |
| 2002/0099376 A1 | 7/2002 | Michelson |
| 2002/0099378 A1 | 7/2002 | Michelson |
| 2002/0116065 A1 | 8/2002 | Jackson |
| 2002/0116165 A1 | 8/2002 | El-Ghoroury |
| 2002/0147454 A1 | 10/2002 | Neto |
| 2002/0147499 A1 | 10/2002 | Shea |
| 2002/0161443 A1 | 10/2002 | Michelson |
| 2002/0165613 A1 | 11/2002 | Lin |
| 2003/0023307 A1 | 1/2003 | Michelson |
| 2003/0045940 A1 | 3/2003 | Eberlein |
| 2003/0060884 A1 | 3/2003 | Fell |
| 2003/0120344 A1 | 6/2003 | Michelson |
| 2003/0149483 A1 | 8/2003 | Michelson |
| 2003/0158553 A1 | 8/2003 | Michelson |
| 2003/0195517 A1 | 10/2003 | Michelson |
| 2003/0195561 A1 | 10/2003 | Carley |
| 2003/0195632 A1 | 10/2003 | Foley |
| 2004/0030336 A1 | 2/2004 | Khanna |
| 2004/0030339 A1 | 2/2004 | Wack |
| 2004/0064185 A1 | 4/2004 | Michelson |
| 2004/0073315 A1 | 4/2004 | Justin |
| 2004/0083005 A1 | 4/2004 | Jacobsson |
| 2004/0117018 A1 | 6/2004 | Michelson |
| 2004/0122518 A1 | 6/2004 | Rhoda |
| 2004/0133203 A1 | 7/2004 | Young |
| 2004/0148028 A1 | 7/2004 | Ferree |
| 2004/0176853 A1 | 9/2004 | Sennett |
| 2004/0210313 A1 | 10/2004 | Michelson |
| 2004/0210314 A1 | 10/2004 | Michelson |
| 2004/0215203 A1 | 10/2004 | Michelson |
| 2004/0220668 A1 | 11/2004 | Eisermann |
| 2004/0220670 A1 | 11/2004 | Eisermann |
| 2004/0225295 A1 | 11/2004 | Zubok |
| 2004/0230308 A1 | 11/2004 | Michelson |
| 2004/0249388 A1 | 12/2004 | Michelson |
| 2004/0254581 A1 | 12/2004 | Leclair |
| 2004/0254644 A1 | 12/2004 | Taylor |
| 2004/0260286 A1 | 12/2004 | Ferree |
| 2005/0004672 A1 | 1/2005 | Pafford |
| 2005/0014919 A1 | 1/2005 | Hatakeyama |
| 2005/0027300 A1 | 2/2005 | Hawkins |
| 2005/0038512 A1 | 2/2005 | Michelson |
| 2005/0038513 A1 | 2/2005 | Michelson |
| 2005/0043802 A1 | 2/2005 | Eisermann |
| 2005/0049600 A1 | 3/2005 | Groiso |
| 2005/0055031 A1 | 3/2005 | Lim |
| 2005/0125065 A1 | 6/2005 | Zucherman |
| 2005/0131545 A1 | 6/2005 | Chervitz |
| 2005/0143747 A1 | 6/2005 | Zubok |
| 2005/0149192 A1 | 7/2005 | Zucherman |
| 2005/0165408 A1 | 7/2005 | Puno |
| 2005/0171606 A1 | 8/2005 | Michelson |
| 2005/0171607 A1 | 8/2005 | Michelson |
| 2005/0177239 A1 | 8/2005 | Steinberg |
| 2005/0187629 A1 | 8/2005 | Michelson |
| 2005/0192586 A1 | 9/2005 | Zucherman |
| 2005/0216089 A1 | 9/2005 | Michelson |
| 2005/0234555 A1 | 10/2005 | Sutton |
| 2005/0273108 A1 | 12/2005 | Groiso |
| 2006/0004453 A1 | 1/2006 | Bartish |
| 2006/0058802 A1 | 3/2006 | Kofoed |
| 2006/0074421 A1 | 4/2006 | Bickley |
| 2006/0079961 A1 | 4/2006 | Michelson |
| 2006/0085071 A1 | 4/2006 | Lechmann |
| 2006/0095136 A1 | 5/2006 | McLuen |
| 2006/0111787 A1 | 5/2006 | Bailie |
| 2006/0116769 A1 | 6/2006 | Marnay |
| 2006/0122702 A1 | 6/2006 | Michelson |
| 2006/0129238 A1 | 6/2006 | Paltzer |
| 2006/0136061 A1 | 6/2006 | Navarro |
| 2006/0142860 A1 | 6/2006 | Navarro |
| 2006/0149377 A1 | 7/2006 | Navarro |
| 2006/0149384 A1 | 7/2006 | Navarro |
| 2006/0167461 A1 | 7/2006 | Hawkins |
| 2006/0178745 A1 | 8/2006 | Bartish |
| 2006/0195097 A1 | 8/2006 | Evans |
| 2006/0212123 A1 | 9/2006 | Lechmann |
| 2006/0241641 A1 | 10/2006 | Albans |
| 2006/0259143 A1 | 11/2006 | Navarro |
| 2006/0259145 A1 | 11/2006 | Navarro |
| 2007/0010890 A1 | 1/2007 | Collazo |
| 2007/0050032 A1 | 3/2007 | Gittings |
| 2007/0055376 A1 | 3/2007 | Michelson |
| 2007/0073404 A1 | 3/2007 | Rashbaum |
| 2007/0093839 A1 | 4/2007 | Beckendorf |
| 2007/0106388 A1 | 5/2007 | Michelson |
| 2007/0118132 A1 | 5/2007 | Culbert |
| 2007/0123903 A1 | 5/2007 | Raymond |

(56) References Cited

U.S. PATENT DOCUMENTS

| | | |
|---|---|---|
| 2007/0142922 A1 | 6/2007 | Lewis |
| 2007/0185375 A1 | 8/2007 | Stad |
| 2007/0233244 A1 | 10/2007 | Lopez |
| 2007/0239278 A1 | 10/2007 | Heinz |
| 2007/0288005 A1 | 12/2007 | Arnin |
| 2007/0288021 A1 | 12/2007 | Rickels |
| 2007/0299529 A1 | 12/2007 | Rhodes |
| 2008/0051901 A1 | 2/2008 | de Villiers |
| 2008/0051902 A1 | 2/2008 | Dwyer |
| 2008/0103598 A1 | 5/2008 | Trudeau |
| 2008/0108997 A1 | 5/2008 | Berrevoets |
| 2008/0132949 A1 | 6/2008 | Aferzon |
| 2008/0140208 A1 | 6/2008 | Zucherman |
| 2008/0147203 A1 | 6/2008 | Cronin |
| 2008/0154377 A1 | 6/2008 | Voellmicke |
| 2008/0167721 A1 | 7/2008 | Bao |
| 2008/0177275 A1 | 7/2008 | Wing |
| 2008/0208345 A1 | 8/2008 | Hurlbert |
| 2008/0249575 A1 | 10/2008 | Waugh |
| 2008/0249623 A1 | 10/2008 | Bao |
| 2008/0269764 A1 | 10/2008 | Blain |
| 2008/0275455 A1 | 11/2008 | Berry |
| 2008/0287957 A1 | 11/2008 | Hester |
| 2009/0005784 A1 | 1/2009 | Blain |
| 2009/0005870 A1 | 1/2009 | Hawkins |
| 2009/0048604 A1 | 2/2009 | Milz |
| 2009/0062921 A1 | 3/2009 | Michelson |
| 2009/0088849 A1 | 4/2009 | Armstrong |
| 2009/0099601 A1 | 4/2009 | Aferzon |
| 2009/0099602 A1 | 4/2009 | Aflatoon |
| 2009/0164020 A1 | 6/2009 | Janowski |
| 2009/0209967 A1 | 8/2009 | Evans |
| 2009/0240333 A1 | 9/2009 | Trudeau |
| 2010/0004747 A1 | 1/2010 | Lin |
| 2010/0069958 A1 | 3/2010 | Sullivan |
| 2010/0185287 A1 | 7/2010 | Allard |
| 2010/0201739 A1 | 8/2010 | Yamaguchi |
| 2010/0204737 A1 | 8/2010 | Bae |
| 2010/0204739 A1 | 8/2010 | Bae |
| 2011/0022176 A1 | 1/2011 | Zucherman |
| 2011/0098819 A1 | 4/2011 | Eisermann |
| 2011/0160766 A1 | 6/2011 | Hendren |
| 2011/0160866 A1 | 6/2011 | Laurence |
| 2011/0166608 A1 | 7/2011 | Duggal |
| 2012/0191204 A1 | 7/2012 | Bae |
| 2012/0215315 A1 | 8/2012 | Hochschuler |
| 2012/0253406 A1 | 10/2012 | Bae |
| 2012/0265259 A1 | 10/2012 | LaPosta |
| 2012/0283837 A1 | 11/2012 | Bae |
| 2013/0013006 A1 | 1/2013 | Rashbaum |
| 2013/0267956 A1 | 10/2013 | Terrill |
| 2014/0039632 A1 | 2/2014 | Hollis |
| 2016/0157906 A1 | 6/2016 | Hollis |
| 2017/0042576 A1 | 2/2017 | Butters |
| 2018/0161167 A1 | 6/2018 | Bae |
| 2018/0250143 A1 | 9/2018 | Su |

FOREIGN PATENT DOCUMENTS

| | | |
|---|---|---|
| EP | 1827318 | 9/2007 |
| EP | 1872746 | 1/2008 |
| EP | 1897517 | 3/2008 |
| EP | 1983941 | 10/2008 |
| EP | 2651341 | 10/2013 |
| EP | 2685938 | 8/2015 |
| EP | 3178448 | 6/2017 |
| WO | WO1993022990 | 11/1993 |
| WO | WO2000025707 | 5/2000 |
| WO | WO2000064360 | 11/2000 |
| WO | WO2001003570 | 1/2001 |
| WO | WO2002003885 | 1/2002 |
| WO | WO2002058593 | 8/2002 |
| WO | WO2003005939 | 1/2003 |
| WO | WO2003039400 | 5/2003 |
| WO | WO2003053290 | 7/2003 |
| WO | WO2003065930 | 8/2003 |
| WO | WO2003092507 | 11/2003 |
| WO | WO2004071359 | 8/2004 |
| WO | WO2004080355 | 9/2004 |
| WO | WO2004089240 | 10/2004 |
| WO | WO2004108015 | 12/2004 |
| WO | WO2005051243 | 6/2005 |
| WO | WO2005074841 | 8/2005 |
| WO | WO2006051547 | 5/2006 |
| WO | WO2006074414 | 7/2006 |
| WO | WO2006086494 | 8/2006 |
| WO | WO2006120505 | 11/2006 |
| WO | WO2006122194 | 11/2006 |
| WO | WO2007028098 | 3/2007 |
| WO | WO2007034310 | 3/2007 |
| WO | WO2007087366 | 8/2007 |
| WO | WO2008014258 | 1/2008 |
| WO | WO2008014453 | 1/2008 |
| WO | WO2008021955 | 2/2008 |
| WO | WO2008034140 | 3/2008 |
| WO | WO2008128367 | 10/2008 |
| WO | WO2009070721 | 6/2009 |
| WO | WO2010039026 | 4/2010 |
| WO | WO2010121002 | 10/2010 |
| WO | WO2011044879 | 4/2011 |
| WO | WO2011090508 | 7/2011 |
| WO | WO2012083205 | 6/2012 |
| WO | WO2012112598 | 8/2012 |

* cited by examiner ically described herein, an aspect of the technology includes a bone implant, including: a first bone-contacting surface; a second bone-contacting surface opposite the first bone-contacting surface; a proxi-
BONE IMPLANTS

CROSS-REFERENCE TO RELATED APPLICATIONS

The present application claims the benefit of:

U.S. Provisional Patent Application Ser. No. 62/398259, entitled BONE IMPLANTS, which was filed on Sep. 22, 2016.

The foregoing is incorporated by reference as though set forth herein in its entirety.

TECHNICAL FIELD

The present disclosure relates to bone implants. More specifically, the present disclosure relates to bone implants which may be used to correct bone abnormalities and/or change bone morphology.

BACKGROUND

A bone osteotomy is a surgical procedure in which bone is cut and/or pieces of the bone are removed to correct abnormalities due to trauma, disease, malformation, and the like. Osteotomies may be used to correct bone morphology in several different planes or fields of reference, including but not limited to: valgus-varus, flexion-extension, internal-external rotation, lengthening-shortening, medial-lateral displacement, dorsal-ventral displacement, and the like. Osteotomies may also be used to correct specific conditions, including but not limited to: (1) variation in growth of paired bones; (2) eccentric epiphysiodesis; (3) diaphyseal angulation due to malunion fractures or growth anomalies; (4) torsional deformities; (5) limb length discrepancies; (6) correction of disease whereby an osteotomy of normal bone may correct a disease condition; and/or (7) any other suitable bone related condition.

A wedge osteotomy is a type of osteotomy in which a wedge-shape may be formed in a bone and/or a wedge-shaped piece of bone may be removed from a bone to correct bone morphology, angular deformity, joint alignment issues, or any other bone related medical condition. For example, a tibial bone osteotomy may be used to realign a knee joint with arthritic damage. In this example, the general goal may be to shift a patient's body weight from one side of the knee joint with arthritic damage to another side of the knee joint where the cartilage may be healthy. A surgeon may accomplish this goal by either inserting or removing a bone wedge in the tibia underneath the knee joint. This may allow the tibia and femur to bend away from the damaged cartilage area and place more weight on the healthy side of the knee joint. Another wedge osteotomy example is a calcaneal bone wedge osteotomy. A calcaneal bone wedge osteotomy may also be used to realign a proximal intertarsal joint and/or a talocalcaneal joint in a foot.

While the bone implants discussed in the present disclosure are described in terms of two example embodiments that correct bone related conditions in the knee and foot respectively, it will be understood that the bone implants of the present disclosure may also be used in other bones, joints, and/or surgical procedures to correct any number of bone related conditions.

SUMMARY

The various systems and methods of the present technology have been developed in response to the present state of the art, and in particular, in response to the problems and needs in the art that have not yet been fully solved by currently available bone implants. The systems and methods of the present technology may provide secure, reliable fixation of bone fragments.

To achieve the foregoing, and in accordance with the technology as embodied and broadly described herein, an aspect of the technology includes a bone implant, including: a first bone-contacting surface; a second bone-contacting surface opposite the first bone-contacting surface; a proximal side; a distal side, wherein the first bone-contacting surface and the second bone-contacting surface diverge away from each other toward the proximal side of the bone implant and converge together toward the distal side of the bone implant; a first protrusion; a second protrusion; an intermediate portion intermediate the first protrusion and the second protrusion, wherein the first protrusion and the second protrusion protrude away from the intermediate portion toward the distal side of the bone implant; and a first recess intermediate the first protrusion and the second protrusion, wherein the first recess is substantially wider than the first protrusion and the second protrusion.

Embodiments of this aspect of the technology may include any or all of the following attributes. The first protrusion, the intermediate portion, and the second protrusion generally form an at least partially crescent shape. The bone implant includes a first channel formed in the first bone-contacting surface of the first protrusion, the first channel configured to receive a first bone anchor; a second channel formed in the first bone-contacting surface of the second protrusion, the second channel configured to receive a second bone anchor; a third channel formed in the second bone-contacting surface of the first protrusion, the third channel configured to receive a third bone anchor; and a fourth channel formed in the second bone-contacting surface of the second protrusion, the fourth channel configured to receive a fourth bone anchor. The bone implant includes a third protrusion intermediate the first protrusion and the second protrusion; and a second recess intermediate the first protrusion and the third protrusion. The first protrusion, the intermediate portion, and the second protrusion generally form an at least partially crescent shape. The bone implant includes a first channel formed in the first bone-contacting surface of the third protrusion, the first channel configured to receive a first bone anchor; a second channel formed in the first bone-contacting surface of the second protrusion, the second channel configured to receive a second bone anchor; a third channel formed in the second bone-contacting surface of the third protrusion, the third channel configured to receive a third bone anchor; and a fourth channel formed in the second bone-contacting surface of the second protrusion, the fourth channel configured to receive a fourth bone anchor.

Another aspect of the technology includes a bone implant system including: a bone implant, including: a first bone-contacting surface; a second bone-contacting surface opposite the first bone-contacting surface; a proximal side; a distal side, wherein the first bone-contacting surface and the second bone-contacting surface diverge away from each other toward the proximal side of the bone implant and converge together toward the distal side of the bone implant; a first protrusion; a second protrusion; an intermediate portion intermediate the first protrusion and the second protrusion, wherein the first protrusion and the second protrusion protrude away from the intermediate portion toward the distal side of the bone implant; and a first recess intermediate the first protrusion and the second protrusion, wherein the first recess is wider than the first protrusion and the second protrusion; and at least one bone anchor coupled to the bone implant, the at least one bone anchor including: a rail configured to slidingly engage the bone implant; a blade spaced apart from the rail and configured to fix the bone anchor to a bone; and at least one leg connecting the blade to the rail, the at least one leg including a cutting edge capable of cutting through bone.

Embodiments of this aspect of the technology may include any or all of the following attributes. The first protrusion, the intermediate portion, and the second protrusion generally form an at least partially crescent shape. The bone implant system includes a first channel formed in the first bone-contacting surface of the first protrusion, the first channel configured to receive a first bone anchor; a second channel formed in the first bone-contacting surface of the second protrusion, the second channel configured to receive a second bone anchor; a third channel formed in the second bone-contacting surface of the first protrusion, the third channel configured to receive a third bone anchor; and a fourth channel formed in the second bone-contacting surface of the second protrusion, the fourth channel configured to receive a fourth bone anchor. The bone implant system includes a third protrusion intermediate the first protrusion and the second protrusion; and a second recess intermediate the first protrusion and the third protrusion. The first protrusion, the intermediate portion, and the second protrusion generally form an at least partially crescent shape. The bone implant system includes a first channel formed in the first bone-contacting surface of the third protrusion, the first channel configured to receive a first bone anchor; a second channel formed in the first bone-contacting surface of the second protrusion, the second channel configured to receive a second bone anchor; a third channel formed in the second bone-contacting surface of the third protrusion, the third channel configured to receive a third bone anchor; and a fourth channel formed in the second bone-contacting surface of the second protrusion, the fourth channel configured to receive a fourth bone anchor.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings in which:

DETAILED DESCRIPTION

Figure 1:
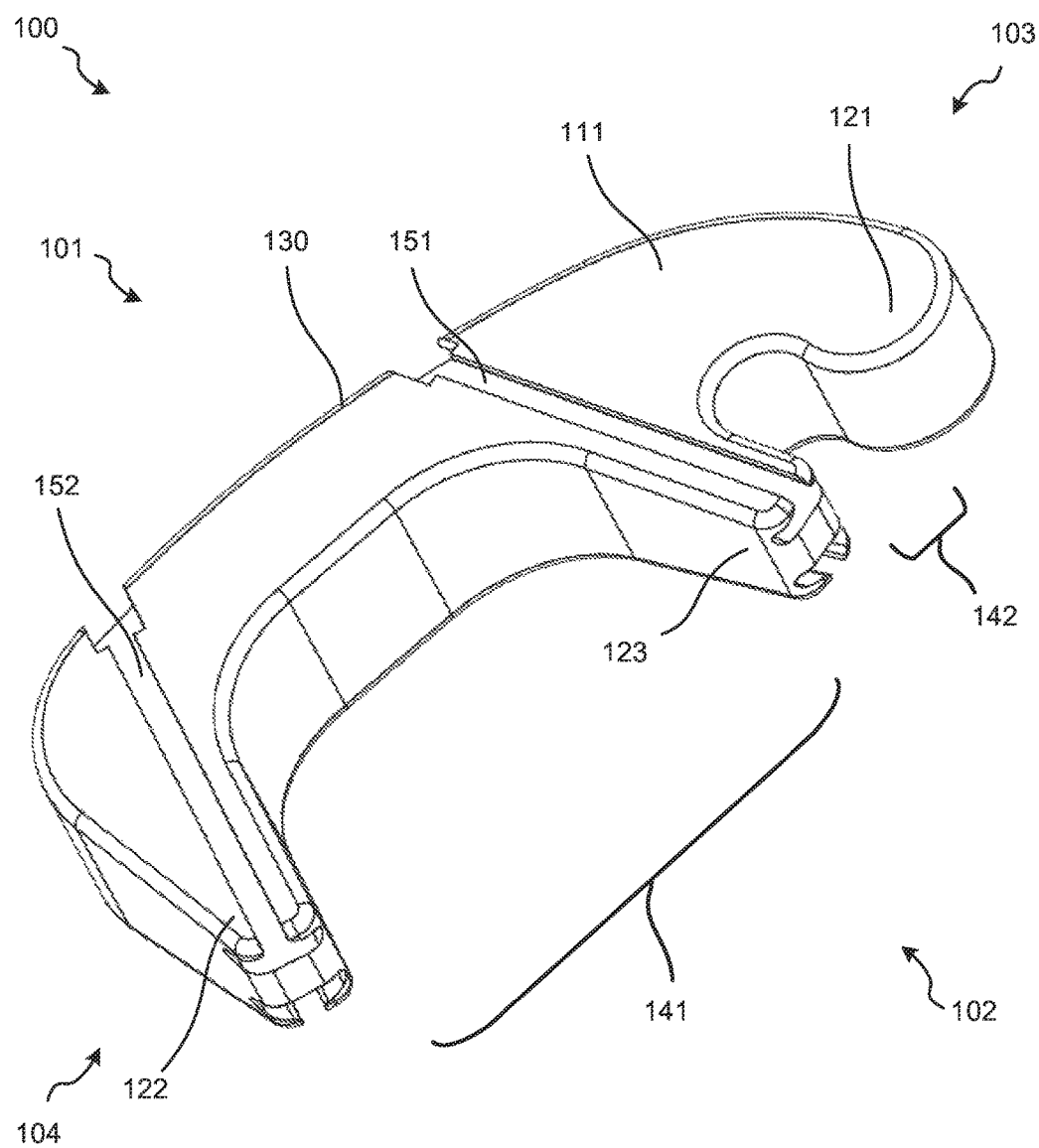
FIG. 1 is an isometric view of a bone implant.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The word "substantially" is used herein to mean "to a great or significant extent."

The word "generally" is used herein to mean "for the most part," in general terms, without regard to exceptions," or "having the overall visual effect."

Standard medical planes of reference and descriptive terminology are employed in this specification. A sagittal plane divides a body into right and left portions. A midsagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body.

Axial means toward a central axis of the body. Abaxial means away from a central axis of the body. Ipsilateral means on the same side of the body. Contralateral means on the opposite side of the body. These descriptive terms may be applied to an animate or inanimate body.

FIGS. 1-3B illustrate various views of a bone implant 100. The bone implant 100 may include a proximal side 101, a distal side 102, an upper side 103, a lower side 104, a first bone-contacting surface 111, and a second bone-contacting surface 112. The second bone-contacting surface 112 may generally be opposite the first bone-contacting surface 111. In at least one embodiment, the first bone-contacting surface 111 and the second bone-contacting surface 112 may be configured to diverge away from each other toward the proximal side 101 of the bone implant 100 and converge together toward the distal side 102 of the bone implant 100. In other embodiments, the first bone-contacting surface 111 and the second bone-contacting surface 112 may be configured to diverge away from each other toward the distal side 102 of the bone implant 100 and converge together toward the proximal side 101 of the bone implant 100. In other embodiments, the first bone-contacting surface 111 and the second bone-contacting surface 112 may be configured to diverge away from each other toward the lower side 104 of the bone implant 100 and converge together toward the upper side 103 of the bone implant 100. In yet further embodiments, the first bone-contacting surface 111 and the second bone-contacting surface 112 may be configured to diverge away from each other toward the upper side 103 of the bone implant 100 and converge together toward the lower side 104 of the bone implant 100. In this manner, the bone implant 100 may generally have a wedge shape that may be formed in one or more directions with a greater height toward one or more sides of the bone implant 100, and a lesser height toward one or more other sides of the bone implant 100.

Figure 2A:
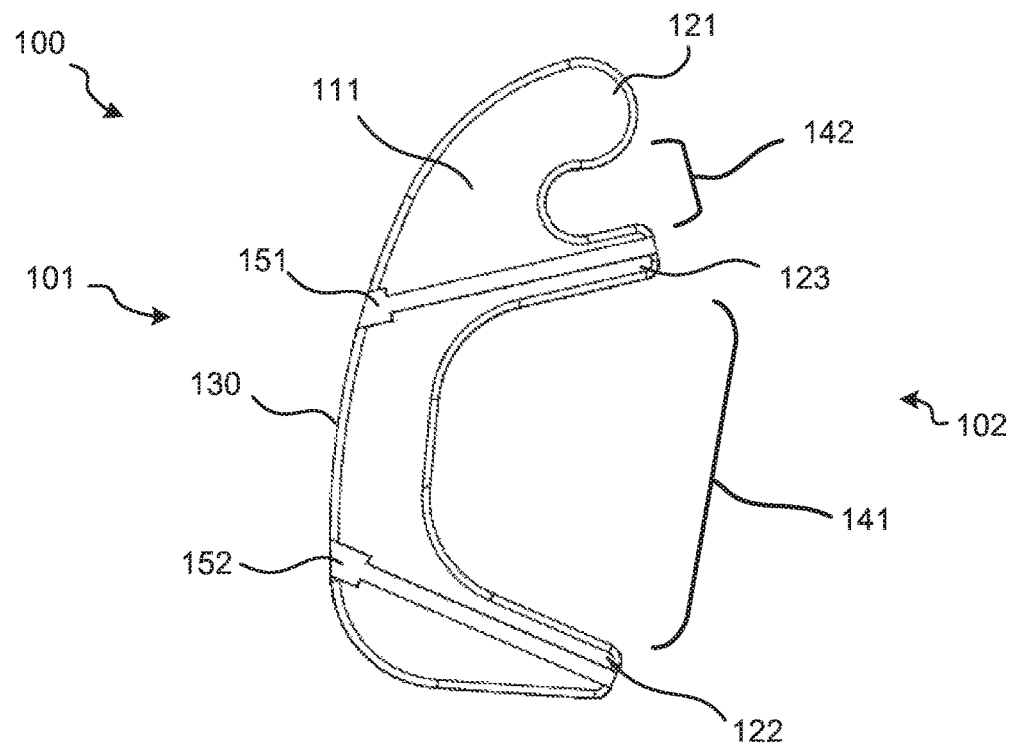
FIG. 2A is a top view of the bone implant of FIG. 1.
Figure 2B:
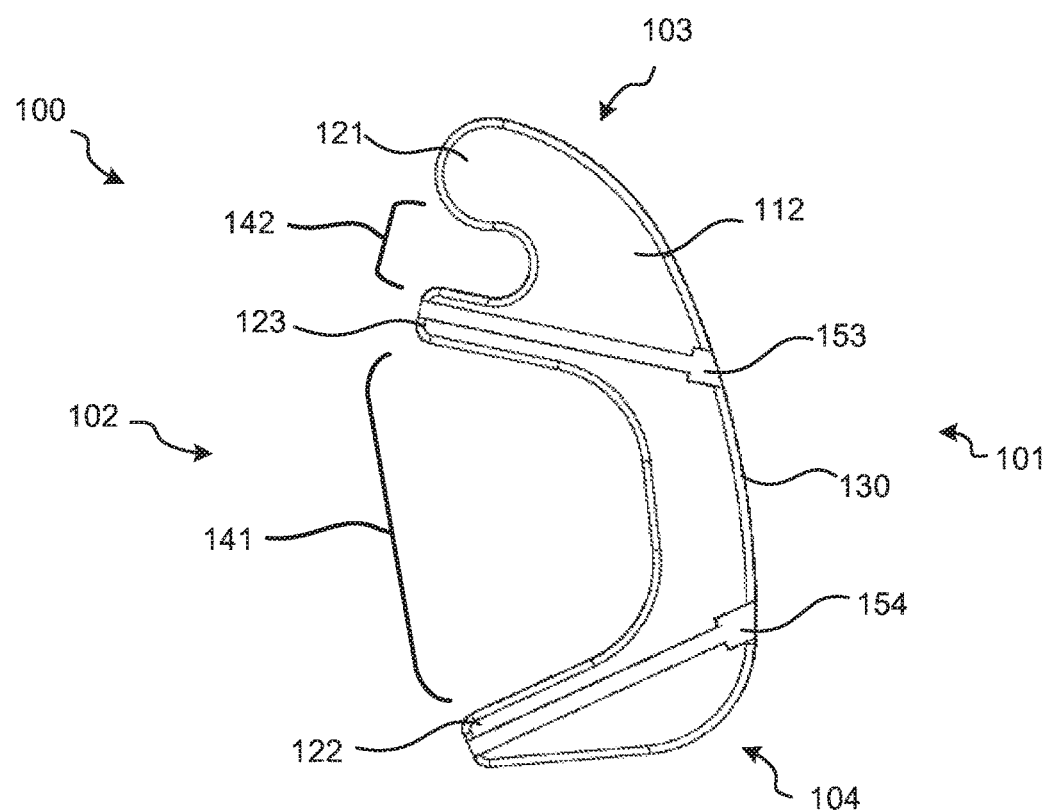
FIG. 2B is a bottom view of the bone implant of FIG. 1.
Figure 3A:
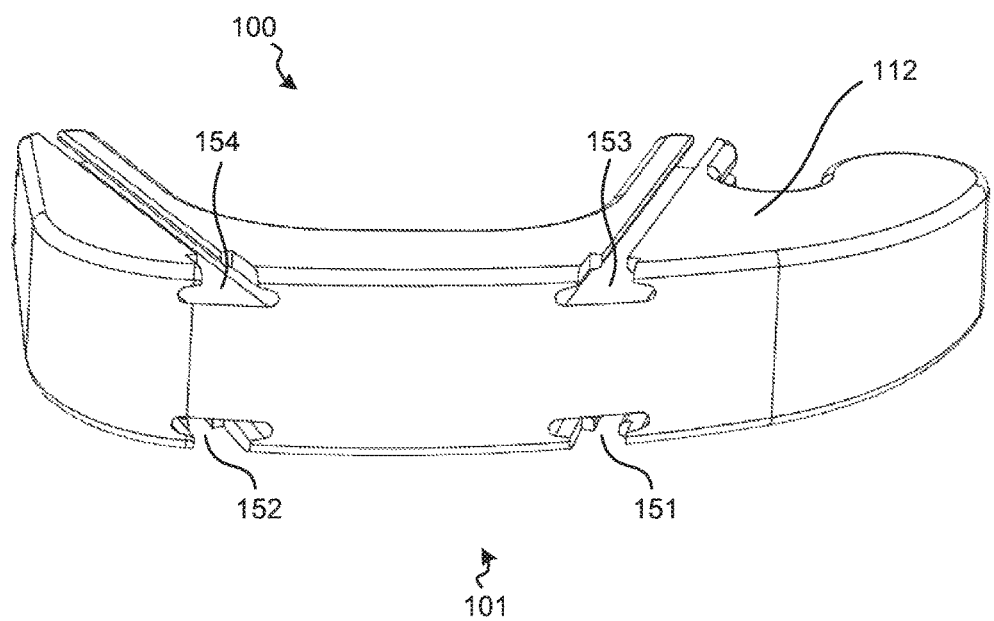
FIG. 3A is an isometric view of a proximal side of the bone implant of FIG. 1.
Figure 3B:
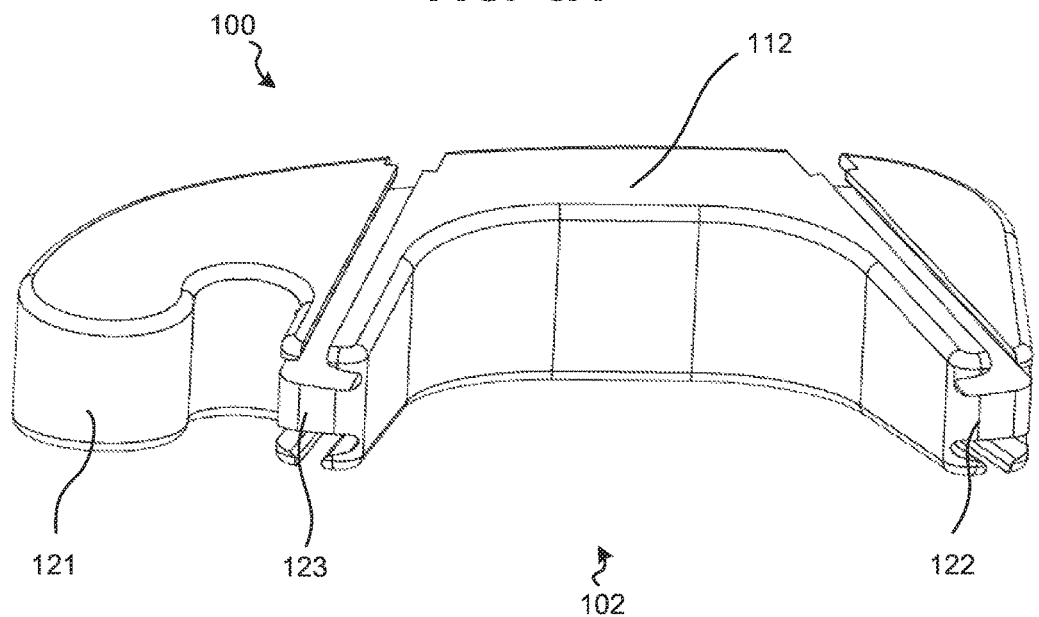
FIG. 3B is an isometric view of a distal side of the bone implant of FIG. 1.
Figure 4A:
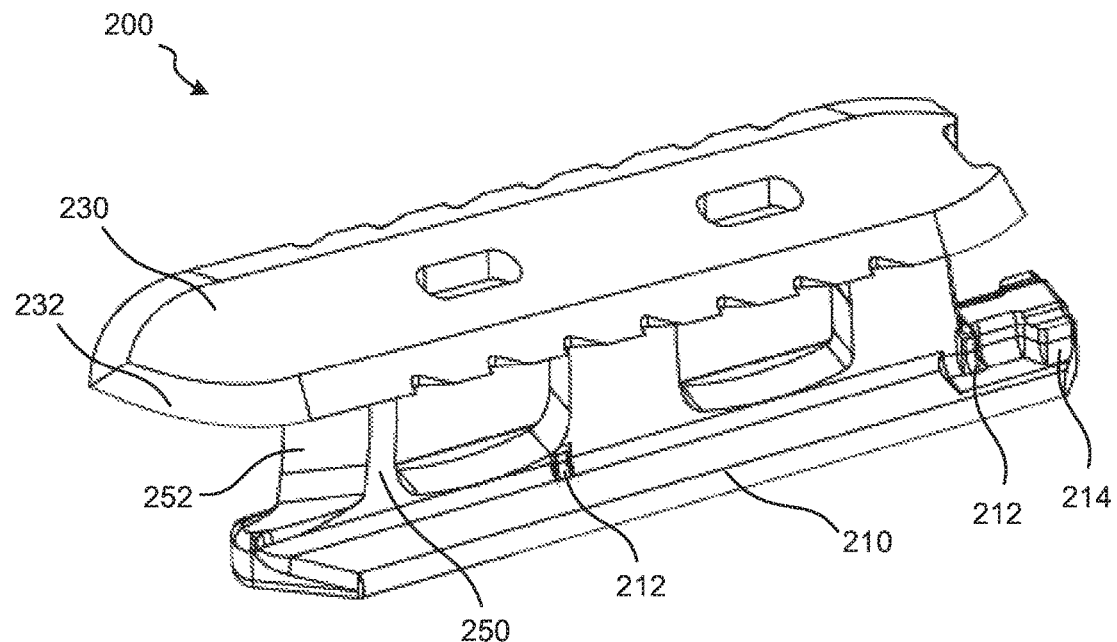
FIG. 4A is an isometric view of a bone anchor.
Figure 4B:
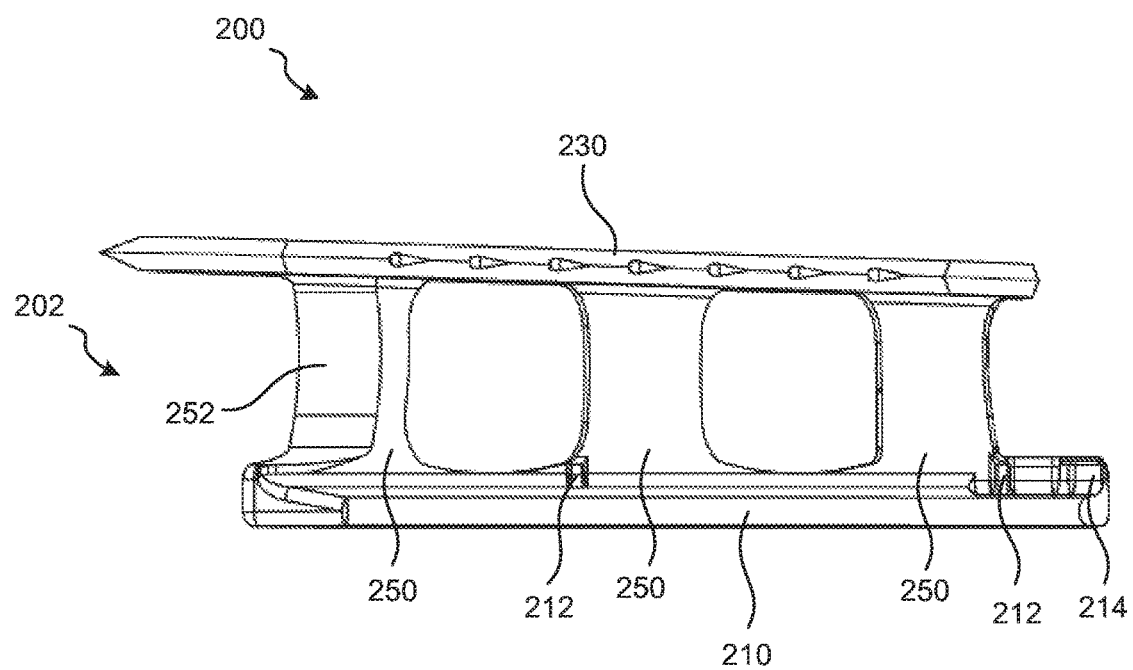
FIG. 4B is a side view of the bone anchor of FIG. 4A.
Figure 5A:
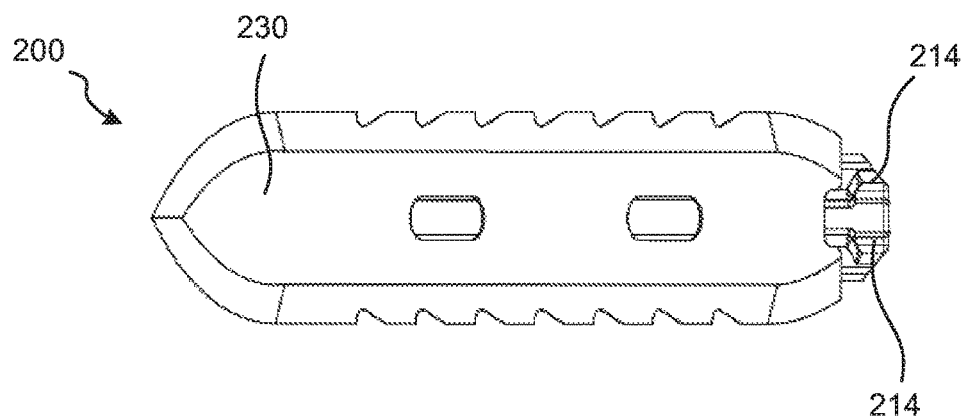
FIG. 5A is a top view of the bone anchor of FIG. 4A.
Figure 5B:
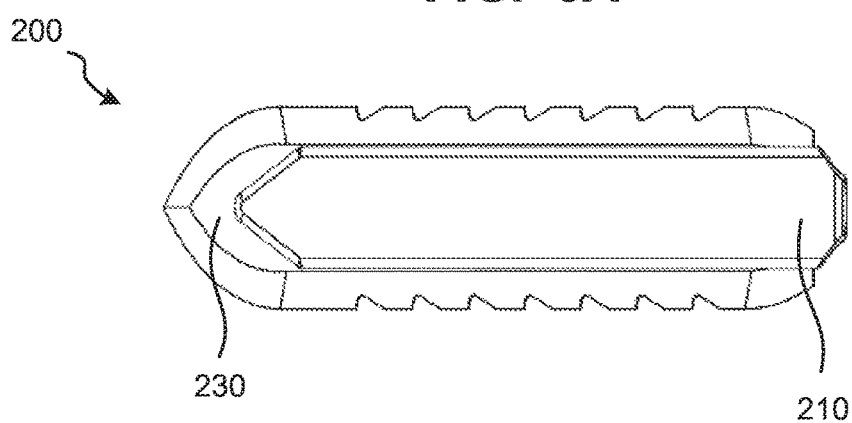
FIG. 5B is a bottom view of the bone anchor of FIG. 4A.
Figure 5C:
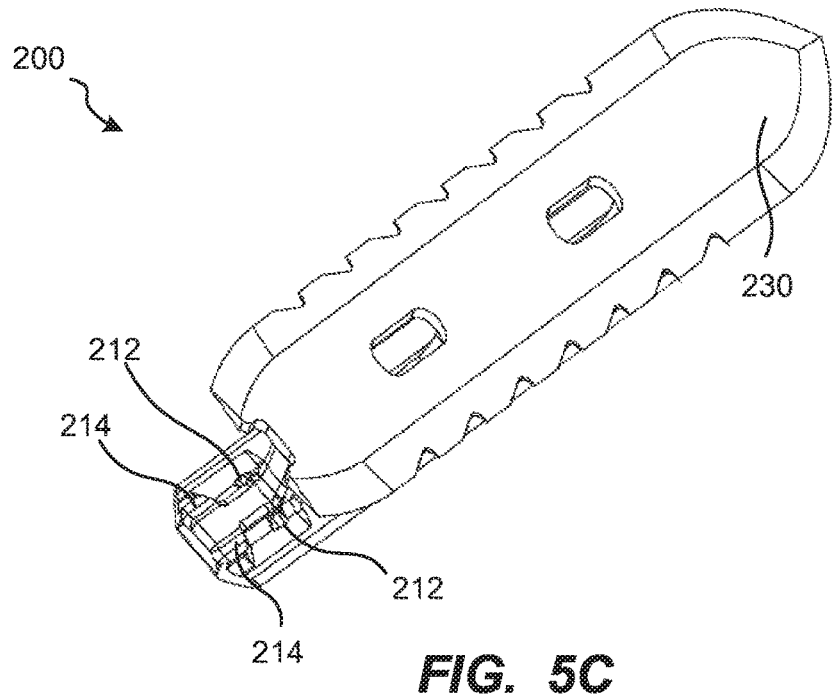
FIG. 5C is an isometric view of the bone anchor of FIG. 4A.

The bone implant 100 may include a first protrusion 121, a second protrusion 122, a third protrusion 123, and an intermediate portion 130. The intermediate portion 130 may be coupled to and intermediate the first protrusion 121, the second protrusion 122, and/or the third protrusion 123. The intermediate portion 130 may form the proximal side 101 of the bone implant 100 as shown, or another side. The third protrusion 123 may be intermediate the first protrusion 121 and the second protrusion 122. The first, second, and third protrusions 121, 122, 123 may protrude away from the intermediate portion 130 toward the distal side 102 of the bone implant 100 as shown, or toward another side. The first protrusion 121, the intermediate portion 130, and the second protrusion 122 may generally form an at least partially crescent shape, as can be seen in the top and bottom views of FIGS. 2A and 2B. Moreover, the first protrusion 121, the intermediate portion 130, and the third protrusion 123 may also generally form an at least partially crescent shape that may be contained within the at least partially crescent shape created by the first protrusion 121, the intermediate portion 130, and the second protrusion 122. The second protrusion 122, the intermediate portion 130, and the third protrusion 123 may also generally form an at least partially crescent shape that may be beside the shape created by the first protrusion 121, the intermediate portion 130, and the third protrusion 123. The first, second, and third protrusions 121, 122, 123 may be parallel or divergent to each other. Referring to FIGS. 2A and 2B, the first protrusion 121 is shown diverging from the second protrusion 122 toward the distal side 102 and converging toward the second protrusion 122 toward the proximal side 101. The first protrusion 121 is shown parallel, or nearly parallel, to the third protrusion 123. The second protrusion 122 is shown diverging from the third protrusion 123 toward the distal side 102 and converging toward the third protrusion 123 toward the proximal side 101.

Figure 7:
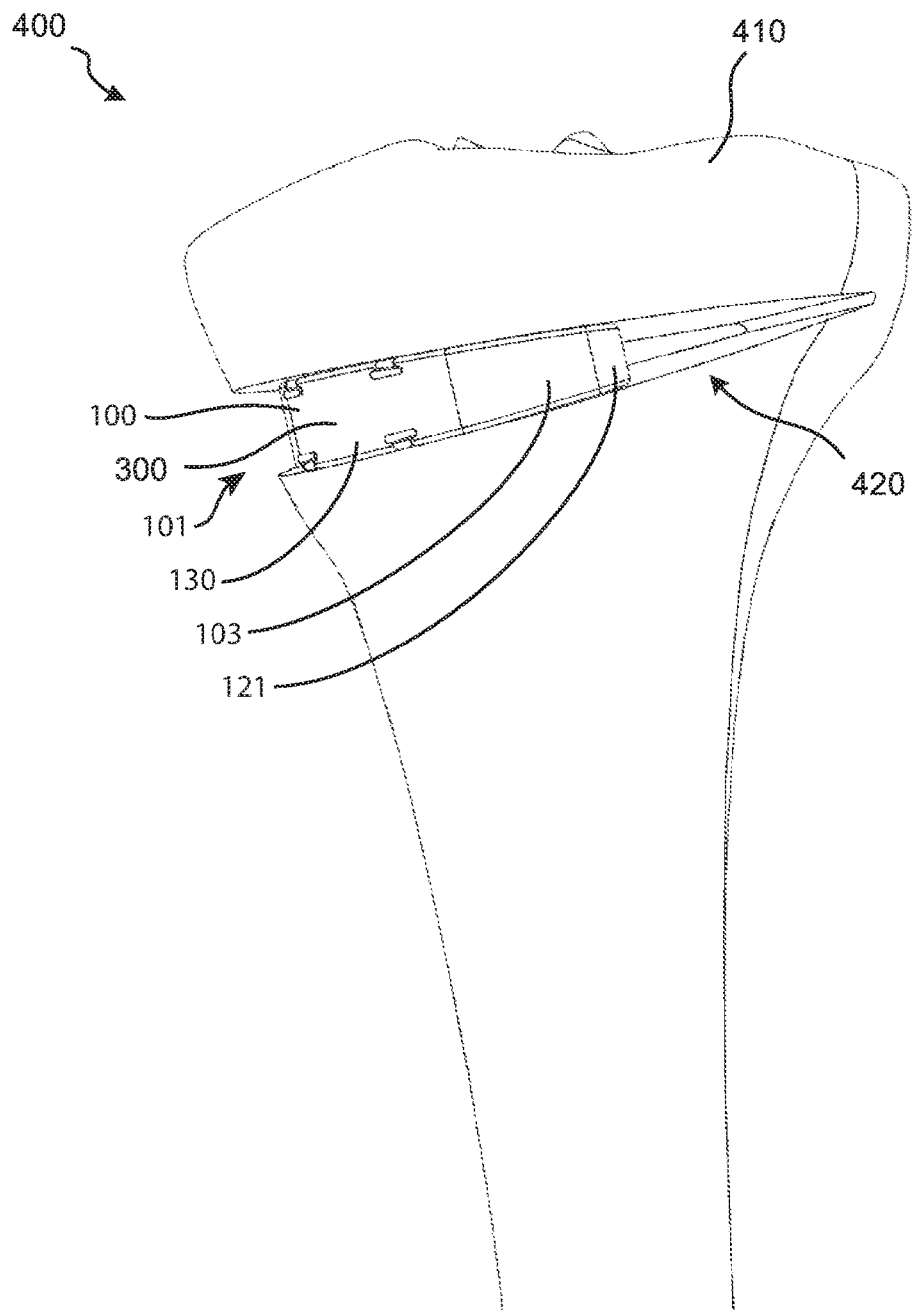
FIG. 7 is an isometric view of the bone implant system of FIG. 6 implanted within a wedge osteotomy formed in a tibial bone.

The first protrusion 121, the intermediate portion 130, and the second protrusion 122 may be designed or configured to rest against cortical bone or dense subcortical bone when the bone implant 100 is implanted. FIG. 7 shows an arrangement in which the first protrusion 121 is against anterior cortical and/or subcortical bone near the tibial tuberosity, the intermediate portion 130 is against antero-medial cortical and/or subcortical bone, and the second protrusion 122 is against medial and/or postero-medial cortical and/or subcortical bone. The third protrusion 123 may be designed or configured to rest against interior trabecular bone, preferably dense trabecular bone. FIG. 7 shows the third protrusion 123 extending into an area of trabecular bone that is posterior to the tibial tuberosity and inferior to (distal to) the intercondyar eminence.

The bone implant 100 may include a first recess 141 that is formed intermediate the first protrusion 121 and the second protrusion 122, and/or intermediate the third protrusion 123 and the second protrusion 122 as shown. The first recess 141 may be substantially wider than the first, second, and/or third protrusions 121, 122, 123. Referring to FIG. 1, width may extend along a direction between the upper side 103 and the lower side 104; more generally, width may extend between the first and second protrusions 121, 122 or parallel to the intermediate portion 130. The width of the first recess 141 may be more than twice the distal width of the first, second, and/or third protrusions 121, 122, 123. The first recess 141 may be more than half the overall width of the bone implant 100. The bone implant 100 may also include a second recess 142 that is formed intermediate the first protrusion 121 and the third protrusion 123. The first recess 141 may also be substantially wider than the second recess 142, in other words, more than twice the distal width of the second recess 142. The width of the second recess 142 may be less than one and a half times the distal width of the first protrusion 121. The first recess 141 and/or the second recess 142 may be designed or configured to receive therapeutic material or agents, such as bone graft, preferably a block or wafer of bone graft.

The bone implant 100 may include a first channel 151 formed in the first bone-contacting surface 111 of the first protrusion 121 and/or the third protrusion 123 as shown. The first channel 151 may extend along the first and/or third protrusion 121, 123 and may extend through the proximal side 101 and the distal side 102 as shown. The first channel 151 may be configured to receive a first bone anchor, which will be discussed in more detail below with reference to FIGS. 4A-5C. The bone implant 100 may include a second channel 152 formed in the first bone-contacting surface 111 of the second protrusion 122. The second channel 152 may extend along the second protrusion 122 and may extend through the proximal side 101 and the distal side 102 as shown. The second channel 152 may be configured to receive a second bone anchor. The bone implant 100 may include a third channel 153 formed in the second bone-contacting surface 112 of the first protrusion 121 and/or the third protrusion 123 as shown. The third channel 153 may extend along the first and/or third protrusion 121, 123 and may extend through the proximal side 101 and the distal side 102 as shown. The third channel 153 may be configured to receive a third bone anchor. The bone implant 100 may include a fourth channel 154 formed in the second bone-contacting surface 112 of the second protrusion 122. The fourth channel 154 may extend along the second protrusion 122 and may extend through the proximal side 101 and the distal side 102 as shown. The fourth channel 154 may be configured to receive a fourth bone anchor. The channels 151, 152, 153, 154 may generally converge toward each other similar to, or identical to, the convergence of the first and second bone-contacting surfaces 111, 112.

The channels 151, 152, 153, 154 may be designed or configured to extend across regions of the bone-contacting surfaces 111, 112 that are adjacent to areas of strong bone when the bone implant 100 is implanted, so that the corresponding bone anchors provide secure fixation when received in the channels and bone. This may influence the design or configuration of the protrusions 121, 122, and/or 123.

FIGS. 4A-5C illustrate various views of a bone anchor 200 that may be used with the bone implants 100, 500. Bone implant 500 will be discussed in more detail below with reference to FIGS. 8-10C. The bone anchor 200 may include a rail 210, a blade 230, and at least one support 250. Three supports are shown. The bone anchor 200 may be elongated and have a generally H-shaped, or T-shaped, cross section.

The rail 210 may be configured to slidingly engage any of the channels of the bone implants 100, 500 to couple the bone anchor 200 to the bone implants 100, 500. In at least one embodiment, the rail 210 may have a dovetail beam shape and may include one or more physical stop features 214 configured to prevent over insertion of the bone anchor 200 into the channel of the bone implant 100, 500. The rail 210 may also include one or more tabs 212 that laterally protrude, or transversely project, from the rail 210. The one or more tabs 212 may also be referred to as laterally protruding tabs, lateral protrusions, and/or interference tabs. The one or more tabs 212 may plastically deform when the rail 210 is inserted into a channel of the bone implants 100, 500. For example, the one or more tabs 212 may deform as the bone anchor 200 is driven into the channel, creating a line-to-line or interference fit between the rail 210 and the bone anchor 200. This material deformation may serve to reduce and/or eliminate any relative motion between the bone anchor 200 and the bone implant 100, 500. The deformation may be characterized as plastic deformation, which may be at least partially irreversible. The deformation may cause galling, spot welding, and/or seizing to occur between the one or more tabs 212 and the channel. Any of these adhesive phenomena may serve to lock the bone anchor 200 to the implant 100, 500. In at least one embodiment, one or more tabs 212 may be located on each side of the rail 210 to provide greater fixation of the bone anchor 200 along the length of the channel. However, in other embodiments a single tab 212, or no tab, may be located on one or more sides of the rail 210. The rail 210 of the bone anchor 200 may be inserted into a channel of the bone implants 100, 500 such that when the rail 210 is inserted into the channel, the one or more tabs 212 may plastically deform, the at least one support 250 may protrude through a bone-contacting surface of the implant 100, 500, and the blade 230 may be carried at a distance from the bone-contacting surface of the implant 100, 500.

The blade 230 may be spaced apart from the rail 210 and configured to fix the bone anchor 200 to a bone. The blade 230 may include a sharpened cutting edge 232 that penetrates the bone when the bone anchor 200 is urged against the bone in a first direction. The sharpened cutting edge 232 may also include one or more serrations that resist removal of the bone anchor 200 from the bone when the bone anchor 200 is pulled from the bone in a second direction. In at least one embodiment, the blade 230 may be biased to diverge away from the rail 210 as the bone anchor 200 is urged against the bone. The biased blade 230 may act to compress the bone against the bone implants 100, 500 as the bone anchor 200 is advanced into the bone.

The at least one support 250 may connect the blade 230 to the rail 210. The at least one support 250 may also include a cutting edge 252 disposed on a leading end 202 of the bone anchor 200 and configured to cut through bone.

Figure 6:
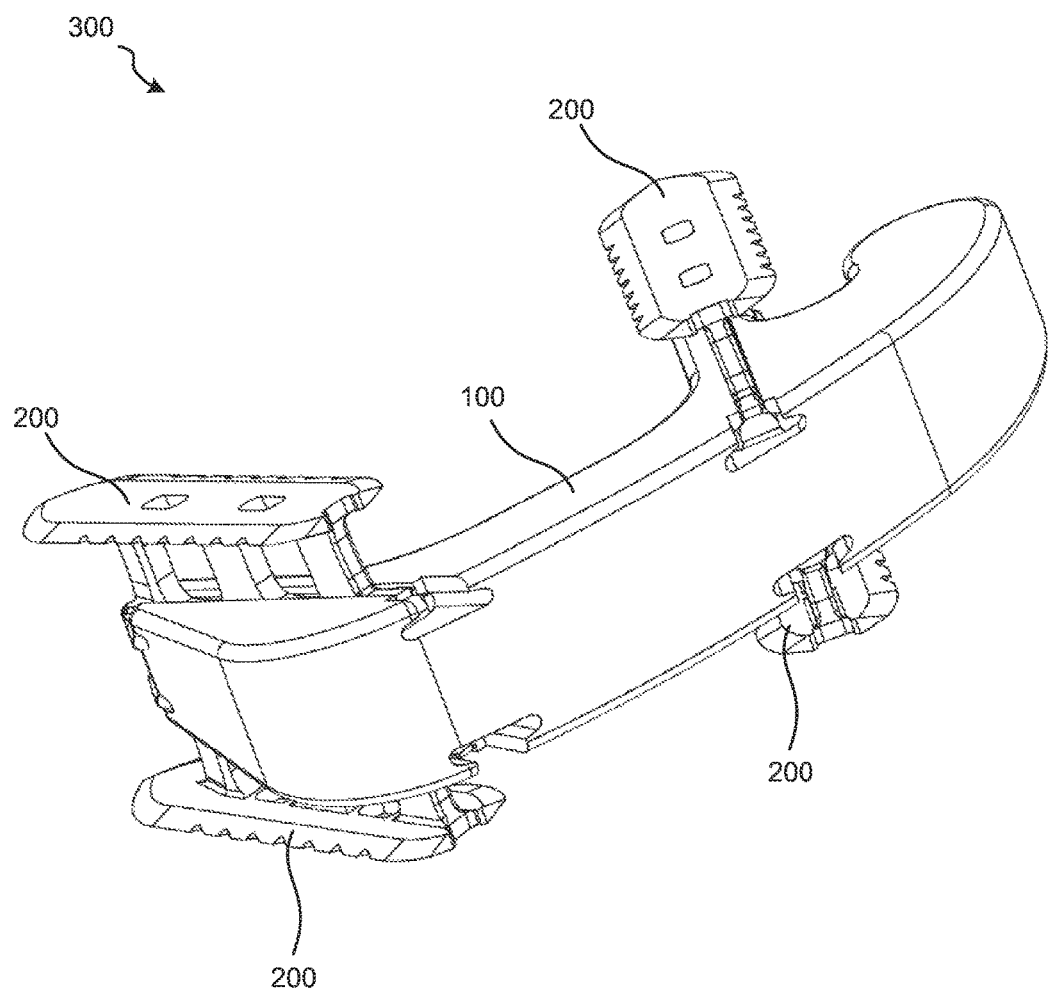
FIG. 6 is an isometric view of a bone implant system including the bone implant of FIG. 1 and the bone anchor of FIG. 4A.

FIG. 6 illustrates a bone implant system 300. The bone implant system 300 may include the bone implant 100 of FIGS. 1-3B coupled to various bone anchors 200, as described in FIGS. 4A-5C. The bone implant system 300 may be implanted within a suitable wedge osteotomy to obtain a desired bone morphology. For example, FIG. 7 illustrates a corrected tibia 400, where the bone implant system 300 has been implanted within a medial wedge osteotomy 420 formed in a tibial bone 410.

FIGS. 8-10C illustrate various views of another bone implant 500. The bone implant 500 may include a proximal side 501, a distal side 502, an upper side 503, a lower side 504, a first bone-contacting surface 511, and a second bone-contacting surface 512. The second bone-contacting surface 512 may generally be opposite the first bone-contacting surface 511. In at least one embodiment, the first bone-contacting surface 511 and the second bone-contacting surface 512 may be configured to diverge away from each other toward the proximal side 501 of the bone implant 500 and converge together toward the distal side 502 of the bone implant 500. In other embodiments, the first bone-contacting surface 511 and the second bone-contacting surface 512 may be configured to diverge away from each other toward the distal side 502 of the bone implant 500 and converge together toward the proximal side 501 of the bone implant 500. In other embodiments, the first bone-contacting surface 511 and the second bone-contacting surface 512 may be configured to diverge away from each other toward the lower side 504 of the bone implant 500 and converge together toward the upper side 503 of the bone implant 500. In yet further embodiments, the first bone-contacting surface 511 and the second bone-contacting surface 512 may be configured to diverge away from each other toward the upper side 503 of the bone implant 500 and converge together toward the lower side 504 of the bone implant 500. In this manner, the bone implant 500 may generally have a wedge shape that may be formed in one or more directions with a greater height toward one or more sides of the bone implant 500, and a lesser height toward one or more other sides of the bone implant 500.

Figure 9A:
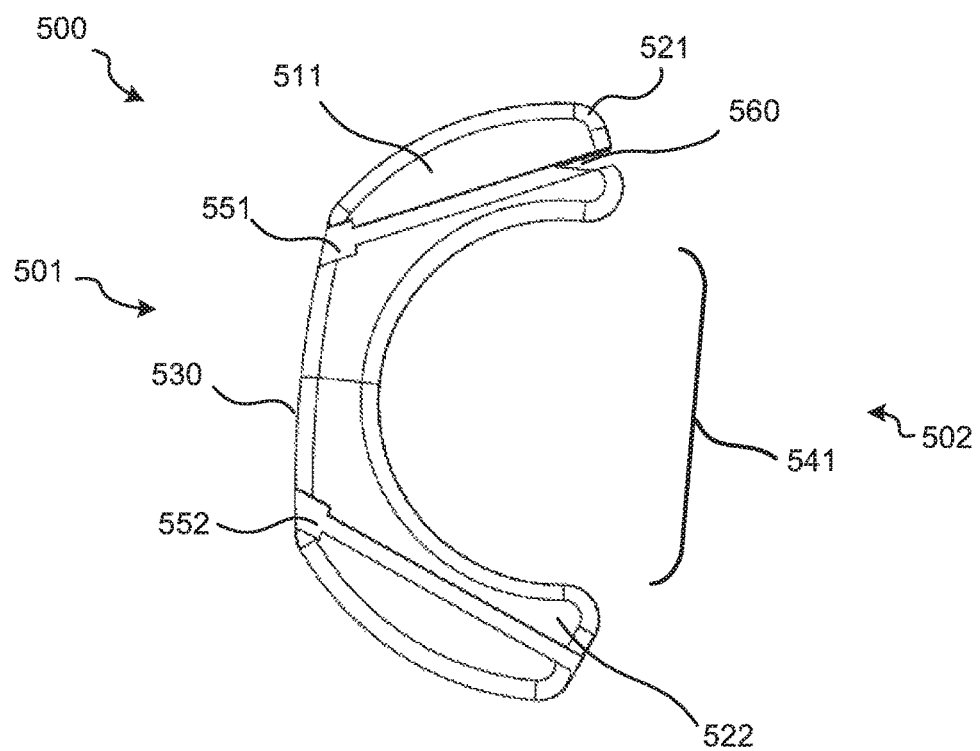
FIG. 9A is a top view of the bone implant of FIG. 8.
Figure 9B:
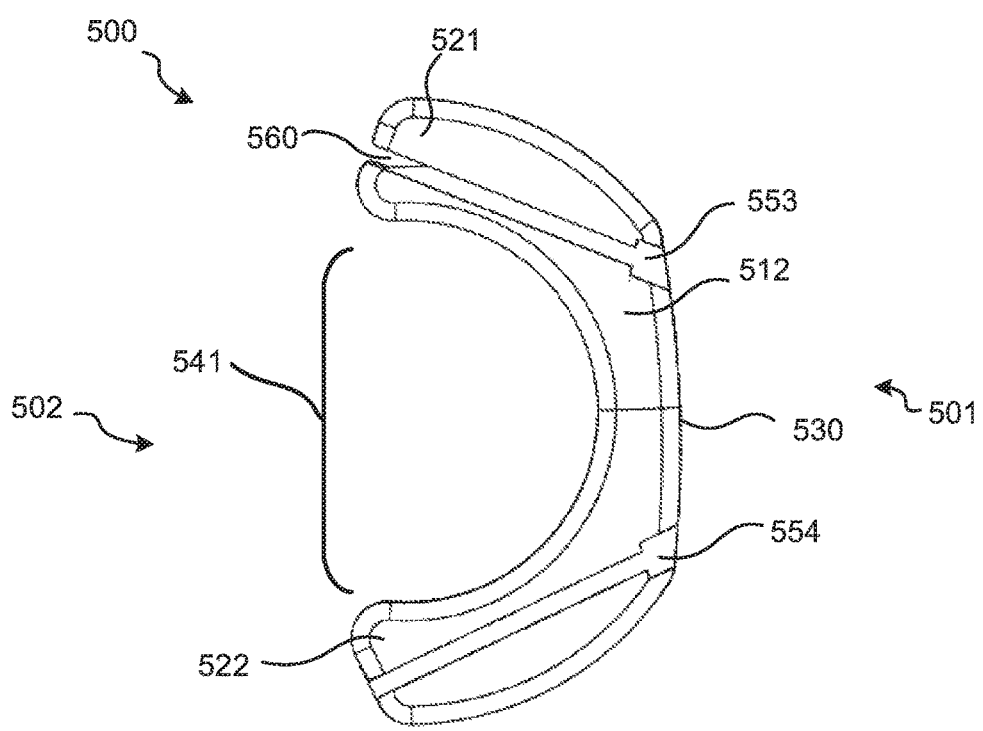
FIG. 9B is a bottom view of the bone implant of FIG. 8.
Figure 10A:
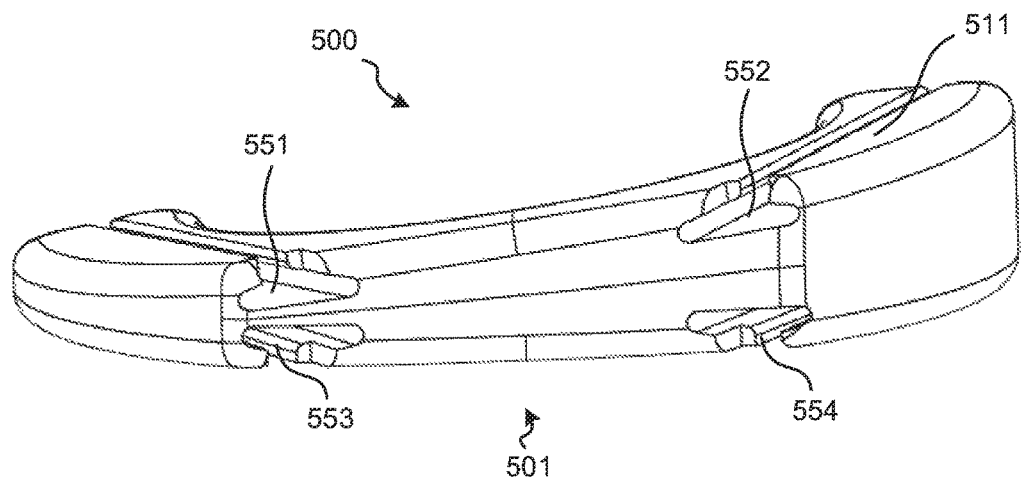
FIG. 10A is an isometric view of a proximal side of the bone implant of FIG. 8.
Figure 10B:
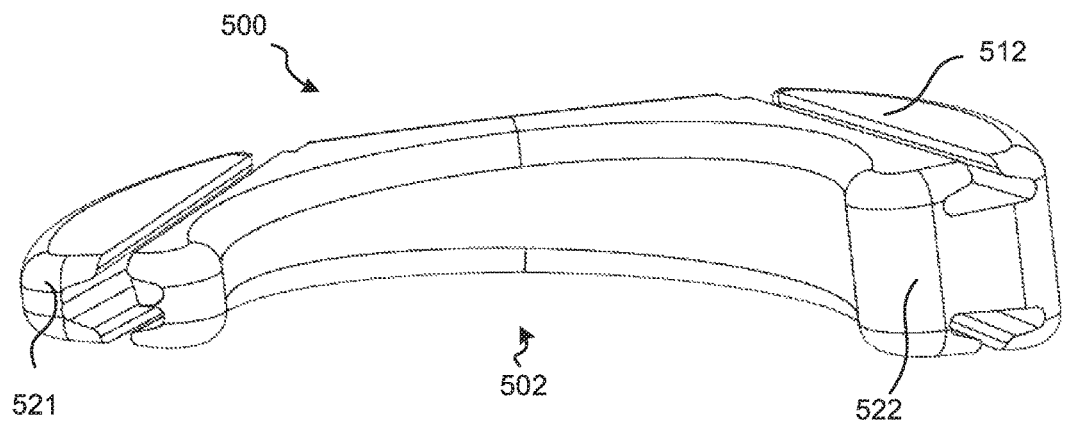
FIG. 10B is an isometric view of a distal side of the bone implant of FIG. 8.
Figure 10C:
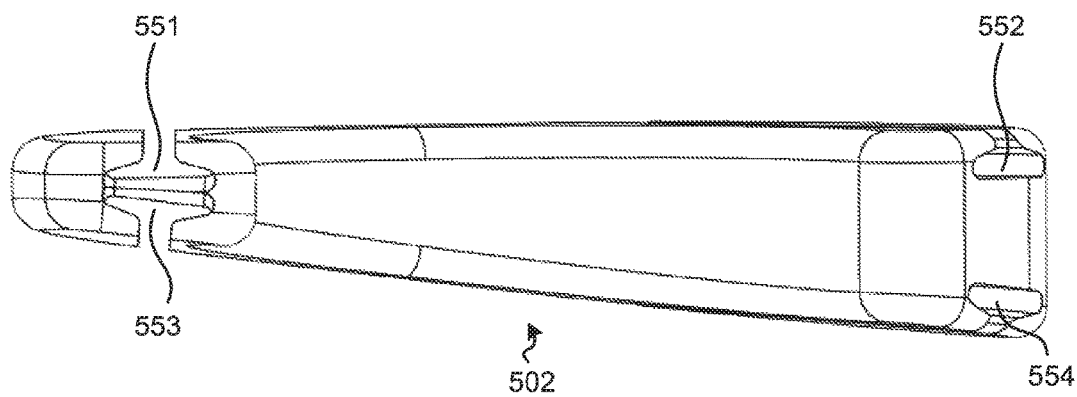
FIG. 10C is a side view of the distal side of the bone implant of FIG. 8.

The bone implant 500 may include a first protrusion 521, a second protrusion 522, and an intermediate portion 530. The intermediate portion 530 may be coupled to and intermediate the first protrusion 521 and the second protrusion 522. The intermediate portion 530 may form the proximal side 501 of the bone implant 500 as shown, or another side. The first and second protrusions 521, 522 may protrude away from the intermediate portion 530 toward the distal side 502 of the bone implant 500, or toward another side. The first protrusion 521, the intermediate portion 530, and the second protrusion 522 may generally form an at least partially crescent shape, as can be seen in the top and bottom views of FIGS. 9A and 9B. The first and second protrusions 521, 522 may be parallel or divergent to each other. Referring to FIGS. 9A and 9B, the first protrusion 521 is shown diverging from the second protrusion 522 toward the distal side 502 and converging toward the second protrusion 522 toward the proximal side 501.

Figure 12:
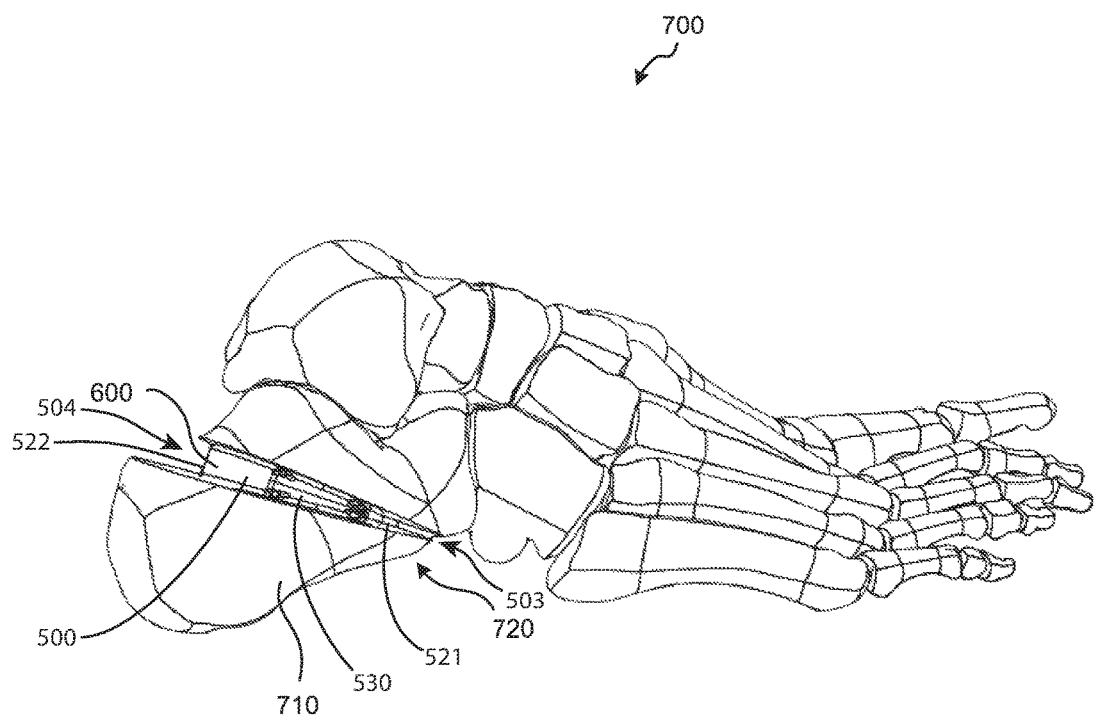
FIG. 12 is an isometric view of the bone implant system of FIG. 11 implanted within a wedge osteotomy formed in a calcaneus bone.

The first protrusion 521, the intermediate portion 530, and the second protrusion 522 may be designed or configured to rest against cortical bone or dense subcortical bone when the bone implant 500 is implanted. FIG. 12 shows an arrangement in which the first protrusion 521 is against anterior-inferior (anterior-plantar) cortical and/or subcortical calcaneal bone, the intermediate portion 530 is against lateral cortical and/or subcortical bone, and the second protrusion 522 is against posterior-superior cortical and/or subcortical bone.

Figure 8:
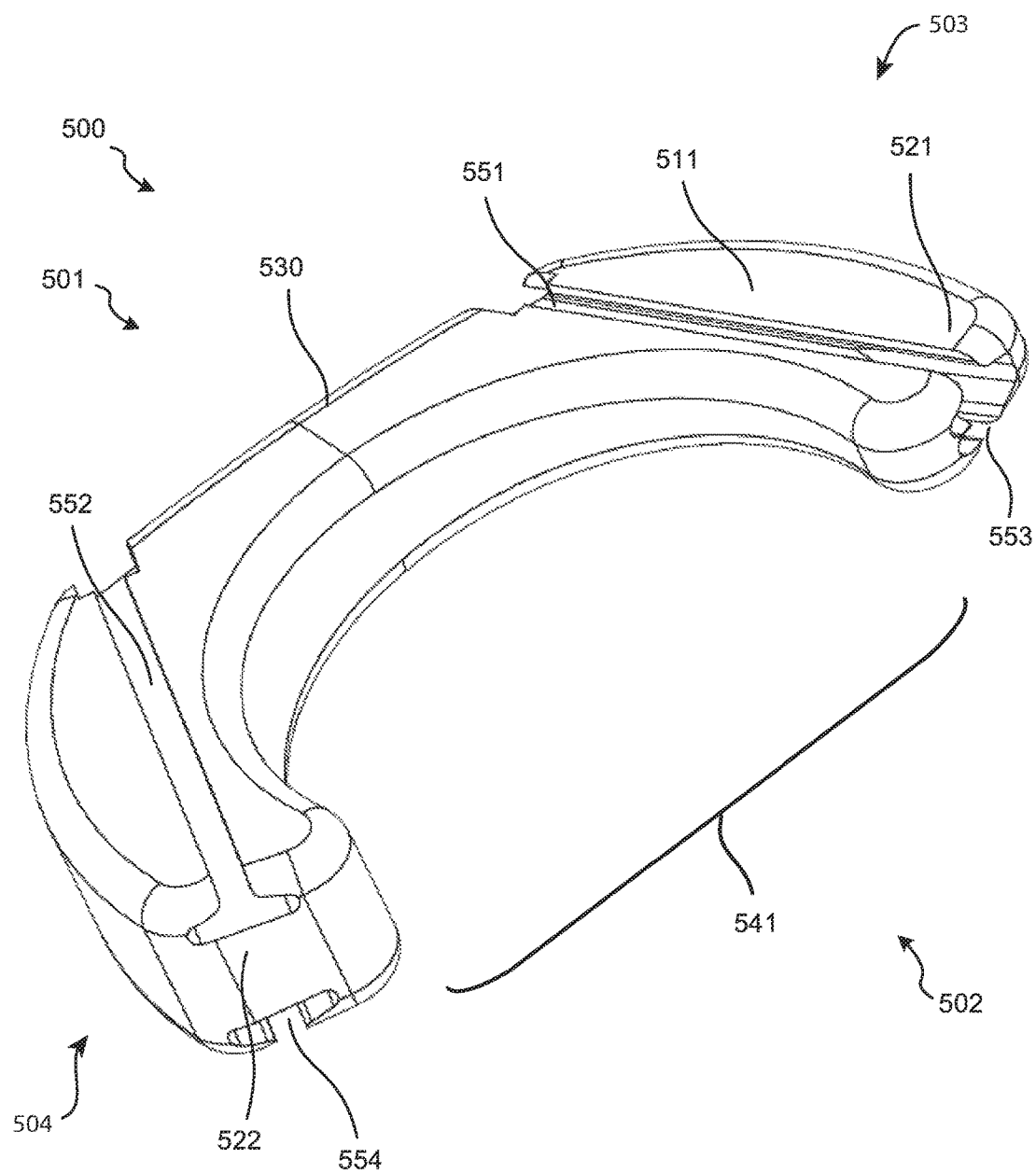
FIG. 8 is an isometric view of another bone implant.

The bone implant 500 may include a first recess 541 that is formed intermediate the first protrusion 521 and the second protrusion 522. The first recess 541 may be arcuate or another concave shape. The first recess 541 may be substantially wider than the first and second protrusions 521, 522. Referring to FIG. 8, width may extend along a direction between the upper side 503 and the lower side 504; more generally, width may extend between the first and second protrusions 521, 522 or parallel to the intermediate portion 530. The width of the first recess 541 may be more than twice the distal width of the first or second protrusion 121, 122. The first recess 541 may be more than half the overall width of the bone implant 500. The first recess 541 may be designed or configured to receive therapeutic material or agents, such as bone graft, preferably a block or wafer of bone graft.

The bone implant 500 may include a first channel 551 formed in the first bone-contacting surface 511 of the first protrusion 521. The first channel 551 may extend along the first protrusion 521 and may extend through the proximal side 501 and the distal side 502 as shown. The first channel 551 may be configured to receive a first bone anchor 200. The bone implant 500 may include a second channel 552 formed in the first bone-contacting surface 511 of the second protrusion 522. The second channel 552 may extend along the second protrusion 522 and may extend through the proximal side 501 and the distal side 502 as shown. The second channel 552 may be configured to receive a second bone anchor 200. The bone implant 500 may include a third channel 553 formed in the second bone-contacting surface 512 of the first protrusion 521. The third channel 553 may extend along the first protrusion 521 and may extend through the proximal side 501 and the distal side 502 as shown. The third channel 553 may be configured to receive a third bone anchor 200. The bone implant 500 may include a fourth channel 554 formed in the second bone-contacting surface 512 of the second protrusion 522. The fourth channel 554 may extend along the second protrusion 522 and may extend through the proximal side 501 and the distal side 502 as shown. The fourth channel 554 may be configured to receive a fourth bone anchor 200.

The channels 551, 552, 553, 554 may generally converge toward each other similar to, or identical to, the convergence of the first and second bone-contacting surfaces 511, 512. In at least one embodiment the channels 551, 553 may converge toward each other, and/or merge together, and/or intersect, before they reach the end of the first protrusion 521, as may be seen in FIGS. 8, 9A, 9B, and 10C. In this embodiment, convergence or intersection of the channels 551, 553 may result in a notch 560 formed in the material of the bone implant 500 between the channels 551, 553. However, it will be understood that in other embodiments, convergence of channels may not result in a notch formed in the material of the bone implant between the converging channels.

The channels 551, 552, 553, 554 may be designed or configured to extend across regions of the bone-contacting surfaces 511, 512 that are adjacent to areas of strong bone when the bone implant 500 is implanted, so that the corresponding bone anchors provide secure fixation when received in the channels and bone. This may influence the design or configuration of the protrusions 521, 522.

Figure 11:
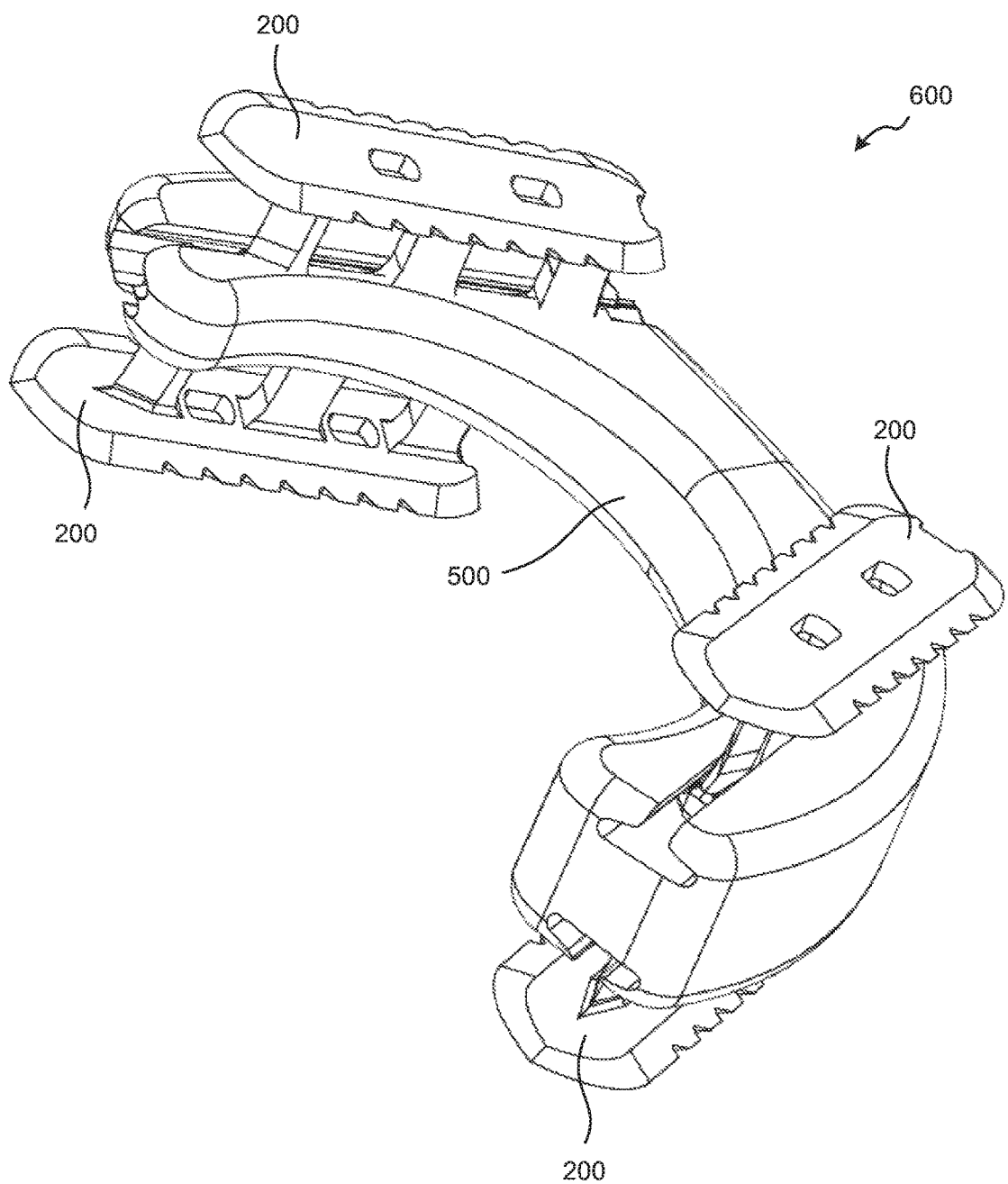
FIG. 11 is an isometric view of another bone implant system including the bone implant of FIG. 8 and the bone anchor of FIG. 4A.

FIG. 11 illustrates a bone implant system 600. The bone implant system 600 may include the bone implant 500 of FIGS. 8-10C coupled to various bone anchors 200, as described in FIGS. 4A-5C. The bone implant system 600 may be implanted within a suitable wedge osteotomy to obtain a desired bone morphology. For example, FIG. 12 illustrates a corrected calcaneus 700, where the bone implant system 600 has been implanted within a wedge osteotomy 720 formed in a calcaneal bone 710. The osteotomy extends from the posterior-superior aspect of the calcaneus 700 to the anterior-inferior aspect of the calcaneus.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment. The word "exemplary" is used herein to mean "serving as an example, instance, or illustration." Any embodiment described herein as "exemplary" is not necessarily to be construed as preferred or advantageous over other embodiments.

Similarly, it will be appreciated that in the above description of embodiments, various features are sometimes grouped together in a single embodiment, figure, or description for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Only elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure herein without departing from the spirit and scope of the disclosure.

The phrases "connected to," "coupled to," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

The invention claimed is:

1. A bone implant, comprising:
   a first bone-contacting surface;
   a second bone-contacting surface opposite the first bone-contacting surface;
   a proximal side;
   a distal side, wherein the first bone-contacting surface and the second bone-contacting surface diverge away from each other toward the proximal side of the bone implant and converge together toward the distal side of the bone implant;
   a first protrusion;
   a second protrusion;
   a third protrusion intermediate the first protrusion and the second protrusion;
   an intermediate portion intermediate the first protrusion and the second protrusion, wherein the first protrusion and the second protrusion protrude away from the intermediate portion toward the distal side of the bone implant;
   a first recess intermediate the first protrusion and the second protrusion, wherein the first recess is substantially wider than the first protrusion and the second protrusion; and
   a second recess intermediate the first protrusion and the third protrusion.

2. The bone implant of claim 1, wherein the first protrusion, the intermediate portion, and the second protrusion generally form an at least partially crescent shape.

3. The bone implant of claim 2, further comprising:
   a first channel formed in the first bone-contacting surface of the first protrusion, the first channel configured to receive a first bone anchor;
   a second channel formed in the first bone-contacting surface of the second protrusion, the second channel configured to receive a second bone anchor;
   a third channel formed in the second bone-contacting surface of the first protrusion, the third channel configured to receive a third bone anchor; and
   a fourth channel formed in the second bone-contacting surface of the second protrusion, the fourth channel configured to receive a fourth bone anchor.

4. The bone implant of claim 1, wherein the first protrusion, the intermediate portion, and the second protrusion generally form an at least partially crescent shape.

5. The bone implant of claim 4, further comprising:
   a first channel formed in the first bone-contacting surface of the third protrusion, the first channel configured to receive a first bone anchor;
   a second channel formed in the first bone-contacting surface of the second protrusion, the second channel configured to receive a second bone anchor;
   a third channel formed in the second bone-contacting surface of the third protrusion, the third channel configured to receive a third bone anchor; and
   a fourth channel formed in the second bone-contacting surface of the second protrusion, the fourth channel configured to receive a fourth bone anchor.

6. A bone implant system comprising:
   a bone implant, comprising:
   a first bone-contacting surface;
   a second bone-contacting surface opposite the first bone-contacting surface;
   a proximal side;
   a distal side, wherein the first bone-contacting surface and the second bone-contacting surface diverge away from each other toward the proximal side of the bone implant and converge together toward the distal side of the bone implant;
   a first protrusion;
   a second protrusion;
   a third protrusion intermediate the first protrusion and the second protrusion;
   an intermediate portion intermediate the first protrusion and the second protrusion, wherein the first protrusion and the second protrusion protrude away from the intermediate portion toward the distal side of the bone implant;
   a first recess intermediate the first protrusion and the second protrusion, wherein the first recess is wider than the first protrusion and the second protrusion; and
   a second recess intermediate the first protrusion and the third protrusion; and
   at least one bone anchor coupled to the bone implant, the at least one bone anchor comprising:
   a rail configured to slidingly engage the bone implant;
   a blade spaced apart from the rail and configured to fix the bone anchor to a bone; and
   at least one leg connecting the blade to the rail, the at least one leg including a cutting edge capable of cutting through bone.

7. The bone implant system of claim 6, wherein the first protrusion, the intermediate portion, and the second protrusion generally form an at least partially crescent shape.

8. The bone implant system of claim 7, further comprising:
   a first channel formed in the first bone-contacting surface of the first protrusion, the first channel configured to receive a first bone anchor;
   a second channel formed in the first bone-contacting surface of the second protrusion, the second channel configured to receive a second bone anchor;
   a third channel formed in the second bone-contacting surface of the first protrusion, the third channel configured to receive a third bone anchor; and
   a fourth channel formed in the second bone-contacting surface of the second protrusion, the fourth channel configured to receive a fourth bone anchor.

9. The bone implant system of claim 6, wherein the first protrusion, the intermediate portion, and the second protrusion generally form an at least partially crescent shape.

10. The bone implant system of claim 9, further comprising:
    a first channel formed in the first bone-contacting surface of the third protrusion, the first channel configured to receive a first bone anchor;
    a second channel formed in the first bone-contacting surface of the second protrusion, the second channel configured to receive a second bone anchor;

a third channel formed in the second bone-contacting surface of the third protrusion, the third channel configured to receive a third bone anchor; and
a fourth channel formed in the second bone-contacting surface of the second protrusion, the fourth channel configured to receive a fourth bone anchor.

* * * * *